(12) United States Patent
Bianchi et al.

(10) Patent No.: US 8,394,416 B2
(45) Date of Patent: Mar. 12, 2013

(54) ONE STEP PROCESS FOR PREPARING CROSS-LINKED POLY(ALLYLAMINE) POLYMERS

(75) Inventors: Sabrina Bianchi, S. Giuliano Terme (IT); Valter Castelvetro, Cascina (IT); Giovanni Marras, Novara (IT); Sonja Bellomi, Novara (IT); Graziano Castaldi, Briona (IT); Gianpiero Ventimiglia, Francavilla Fontana (IT)

(73) Assignee: Chemo Ibérica, S.A., Barcelona (ES)

( * ) Notice: Subject to any disclaimer, the term of this patent is extended or adjusted under 35 U.S.C. 154(b) by 405 days.

(21) Appl. No.: 12/668,758

(22) PCT Filed: Jul. 16, 2008

(86) PCT No.: PCT/EP2008/059303
§ 371 (c)(1),
(2), (4) Date: Jan. 12, 2010

(87) PCT Pub. No.: WO2009/010531
PCT Pub. Date: Jan. 22, 2009

(65) Prior Publication Data
US 2010/0183732 A1 Jul. 22, 2010

(30) Foreign Application Priority Data
Jul. 17, 2007 (EP) .................... 07112604

(51) Int. Cl.
*A61K 9/50* (2006.01)
*C08F 6/00* (2006.01)
*C08F 8/00* (2006.01)
*C08C 19/32* (2006.01)
*C08G 65/48* (2006.01)

(52) U.S. Cl. ........ 424/501; 528/480; 525/351; 525/385; 525/393

(58) Field of Classification Search .................. None
See application file for complete search history.

(56) References Cited

U.S. PATENT DOCUMENTS

| 4,605,701 | A | | 8/1986 | Harada et al. |
| 5,496,545 | A | * | 3/1996 | Holmes-Farley et al. . 424/78.11 |
| 6,083,495 | A | | 7/2000 | Holmes-Farley et al. |
| 6,362,266 | B1 | | 3/2002 | Buchholz et al. |
| 6,509,013 | B1 | | 1/2003 | Holmes-Farley et al. |
| 6,733,780 | B1 | | 5/2004 | Tyler et al. |
| 6,858,203 | B2 | | 2/2005 | Holmes-Farley et al. |
| 7,014,846 | B2 | | 3/2006 | Holmes-Farley et al. |
| 2002/0028887 | A1 | | 3/2002 | Hirano et al. |
| 2005/0131138 | A1 | * | 6/2005 | Connor et al. ................ 524/612 |
| 2006/0171916 | A1 | | 8/2006 | Holmes-Farley et al. |
| 2007/0190135 | A1 | * | 8/2007 | Matsuda et al. .............. 424/464 |

FOREIGN PATENT DOCUMENTS

| CN | 1150435 A | 5/1997 |
| EP | 764 174 A1 | 3/1997 |
| EP | 0716 606 B1 | 8/2001 |
| EP | 1 379 258 | 10/2002 |
| WO | WO 95/05184 A2 | 2/1995 |
| WO | WO 2006/050315 A2 | 5/2006 |
| WO | WO 2007/035313 A2 | 3/2007 |

OTHER PUBLICATIONS

Cosevelam "Wlchol Colesevelam", Sep. 28, 2000, accessed from: http://tess2.uspto.gov/bin/showfield?f=doc&state=4004:svan21.3.7, pp. 1-2.*
CAS Registry file, "Document 132:284260, accession 2000:260358", accessed from CAS registry/CAPLUS, available on May 9, 2000, pp. 1-3.*
K. B Sharpless. et al., *J. Org. Chem.*, (1989), 54, 1295-1304.
J. R. Mazzeo et al.,*Journal of Pharmaceutical and Biomedical Analysis*, 19 (1999) 911-915.

* cited by examiner

*Primary Examiner* — Michael G Hartley
*Assistant Examiner* — Lance Rider
(74) *Attorney, Agent, or Firm* — ProPat, L.L.C.

(57) ABSTRACT

The present invention relates to a novel one step process for preparing cross-linked poly(allylamine) polymers or salts thereof using the novel cross-linking agent of Formula (IV).

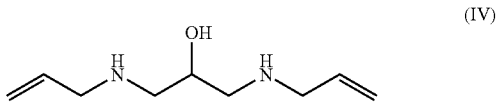

(IV)

This invention also relates to the compound of Formula (IV) as well as to a process to obtain it. The cross-linked poly (allylamine) polymers of the invention are useful in medicine as substrate-binding polymers.

19 Claims, No Drawings

ONE STEP PROCESS FOR PREPARING CROSS-LINKED POLY(ALLYLAMINE) POLYMERS

CROSS-REFERENCE TO RELATED APPLICATIONS

This application is being filed under Rule 1.371 as a National Stage Application of pending International Application No. PCT/EP2008/059303 filed Jul. 16, 2008, which claims priority to parent application European Patent Application No. 07112604.9, filed Jul. 17, 2007. Both International Application No. PCT/EP2008/059303 and European Patent Application No. 07112604.9 are hereby incorporated by reference herein in their entirety.

FIELD OF THE INVENTION

The present invention relates to a novel one step process for preparing cross-linked poly(allylamine) polymers or salts thereof using the novel cross-linking agent of Formula (IV).

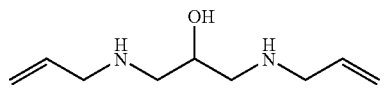
(IV)

This invention also relates to the compound of Formula (IV) as well as to a process to obtain it.

The cross-linked poly(allylamine) polymers of the invention show a controlled particle size and are useful in medicine as substrate-binding polymers.

BACKGROUND OF THE INVENTION

In the recent years, fixation of physiologically active molecules, such as pharmaceutical molecule, enzyme molecule and the like, on a polymeric support is extensively studied.

Cross-linked poly(allylamine) polymers have found many therapeutic applications as substrate-binding polymers:

a) in hyperphosphatemia, phosphate-binding polymers are provided for removing phosphate from the gastrointestinal tract by oral administration;
b) in hypercholesterolemia, bile acid-binding polymers are used as effective treatment for removing bile salts from a subject and thereby reducing the subject's cholesterol level. Because the sole biological precursor to bile salts is cholesterol, the metabolism of cholesterol to make bile salts is accompanied by a simultaneous reduction in the cholesterol in the subject.

Hyperphosphatemia is one of the major complications of hemodialysis subjects and plays a key role in the pathogenesis of cardiovascular calcification and secondary hyperparathyroidism. Hyperphosphatemia, especially if present over extended periods of time, leads to severe abnormalities in calcium and phosphorus metabolism, often manifested by aberrant calcification in joints, lungs, and eyes. Therapeutic efforts to reduce serum phosphate include dialysis, reduction in dietary phosphate, and oral administration of insoluble phosphate binders to reduce gastrointestinal absorption. Dialysis and reduced dietary phosphate are usually insufficient to adequately reverse hyperphosphatemia, so the use of phosphate binders is routinely required to treat these subjects. Phosphate binders include calcium or aluminium salts, or organic polymers that act as ion exchange resins.

Calcium salts have been widely used to bind intestinal phosphate and prevent absorption. Different types of calcium salts have been utilized for phosphate binding. The major problem with all of these therapeutics is the hypercalcemia that causes serious side effects such as cardiac arrhythmias, renal failure, and skin and visceral calcification. Frequent monitoring of serum calcium levels is required during therapy with calcium-based phosphate binders.

Aluminium-based phosphate binders have also been used for treating hyperphosphatemia, but prolonged use of aluminium gels leads to accumulations of aluminium, and often to aluminium toxicity, accompanied by such symptoms as encephalopathy, osteomalacia, and myopathy.

Among the most widely used phosphate binders, Sevelamer hydrochloride, an organic polymer that acts as ion-exchange resin, shows the best characteristics of low toxicity and binding efficiency.

Sevelamer hydrochloride is a compound of Formula (III),

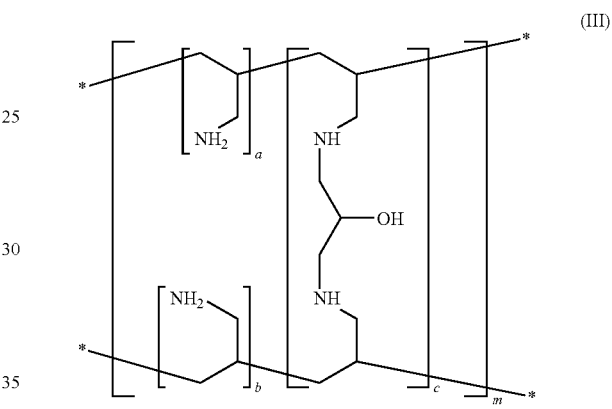

a poly(allylamine) cross-linked with epichlorohydrin, which is disclosed in EP 716 606 B1 (whose United States equivalent is U.S. Pat. No. 4,255,431) and marketed under the trade name RENAGEL®. Sevelamer hydrochloride is a polycation polymer and binds phosphorus in the gastrointestinal tract to facilitate phosphorus excretion in faeces, thereby inhibiting phosphorus absorption from the gut, and thereby lowering the plasma phosphorus concentration.

Hyperphosphatemia and metabolic acidosis frequently accompanies diseases associated with inadequate renal function. Current treatments for hyperphosphatemia do not address the issue of metabolic acidosis; its consequences can be serious. The human body is constantly gaining H+ ions from the metabolism of sugars, fats, protein and lactic acid (produced under anaerobic metabolism). To maintain a constant pH the body must excrete H+ ions. Decreased excretion of H+ ions occurs in patients suffering from renal disease or renal failure, which results in metabolic acidosis and, hence, a low blood pH due to excess H+ ions. To treat metabolic acidosis, Sevelamer carbonate represents a good alternative. Sevelamer carbonate is a poly(allylamine) polymer cross-linked with epichlorohydrin, disclosed in EP 716 606 B1 (whose United States equivalent is U.S. Pat. No. 4,255,431), and marketed under the trade name RENVELA®.

The patent application WO 2007035313 discloses a powder formulation comprising a pharmaceutically acceptable anionic stabilizer and cross-linked poly(allylamine) polymers or a pharmaceutically acceptable salt thereof, such as Sevelamer carbonate, mixed with the anionic stabilizer. The powder formulation contains less than 5 wt % of particles having a particle size more than 300 μm and less than 5 wt % of particles having a particle size less than 10 μm.

Reabsorption of bile acids from the intestine conserves lipoprotein cholesterol in the bloodstream. Conversely, blood cholesterol levels can be diminished by reducing reabsorption of bile acids. One method of reducing the amount of bile acids that are reabsorbed and, thus, reducing serum cholesterol is the oral administration of compounds that sequester the bile acids and cannot themselves be absorbed. The sequestered bile acids consequently either decompose by bacterial action or are excreted. Compounds which have been suggested for bile acids sequestration include various ion exchange polymers. One such polymer is Colesevelam hydrochloride, a poly(allylamine) hydrochloride cross-linked with epichlorohydrin and alkylated with 1-bromodecane and (6-bromohexyl)-trimethylammonium bromide, disclosed in EP 764.174 B1 (whose United States equivalents are U.S. Pat. Nos. 5,693,675 and 5,679,717), and marketed under the trade name WELCHOL®. Colesevelam hydrochloride is a non-absorbed, lipid-lowering polymer that binds bile acids in the intestine, impeding their reabsorption.

As said above, phosphate-binding polymers, such as Sevelamer hydrochloride, Sevelamer carbonate, and bile acid-binding polymers, such as Colesevelam hydrochloride, are cross-linked polymers characterized by allylamine as repeating unit, "poly(allylamine) polymers", or a salt thereof. Several methods have been used to prepare cross-linked poly(allylamine) polymers.

The methods disclosed in EP 716.606 B1 (whose United States equivalent is U.S. Pat. No. 4,255,431), to obtain cross-linked poly(allylamine) polymers, such as Sevelamer hydrochloride, involves a two step process consisting of:
a) preparing poly(allylamine) hydrochloride from allylamine;
b) neutralizing with NaOH and cross-linking poly(allylamine) with epichlorohydrin by an alkylation reaction.

U.S. Pat. No. 6,362,266 discloses a process for producing a cross-linked poly(allylamine) polymer having reduced cohesiveness from an aqueous solution of a washed cross-linked poly(allylamine) polymer treated with a surfactant.

U.S. Pat. No. 4,605,701 discloses a process for producing a small-globular cross-linked polymer of monoallylamine through a post-polymerization reaction of a crosslinking agent with the monoallylamine homopolymer in an inverse emulsion.

All these methods involve a non economical two steps process and usually the poly(allylamine) polymers obtained are a gel like substances.

When a gel like substance is obtained, mechanical or chemical processes (e.g. grinding, slurring, lyophilisation, ...) are further needed to transform a gel like substance in a solid state.

The cross-linking agent of choice in the prior art is epichlorohydrin, a harmful and suspect carcinogenic substance. Further, the cross-linking of poly(allylamine) with epichlorohydrin or with any other suitable difunctional molecule may lead to a poor compositional homogeneity of the final cross-linked polymer. This is particularly true if the difunctional cross-linking molecule is not soluble in the aqueous solvent that is the solvent of choice for the polymerisation of allylamine, and if the two functional groups of said molecule have different reactivity. Furthermore, purification of the cross-linked product from any unreacted cross-linking agent is a costly and possibly poorly efficient procedure.

Therefore, a novel process for preparing cross-linked poly(allylamine) polymers, a method applicable to producing a variety of hyperbranched polymers by means of a single step consisting of free radical polymerization in batch, semi-continuous or, even more preferably, a continuous reactor would be highly desirable.

An object of the present invention is to provide a novel, efficient, economic and commercially useful, one step process for preparing cross-linked poly(allylamine) polymers or salts thereof, that avoid the above-mentioned disadvantages.

SUMMARY OF THE INVENTION

The present invention relates to a novel one step process for preparing cross-linked polymers or salts thereof comprising a repeating unit of Formula (I),

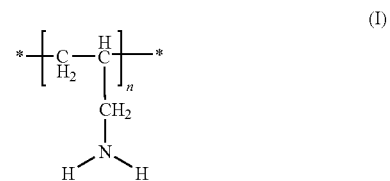

and/or Formula (II),

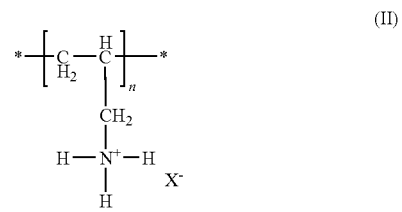

wherein n is an integer and $X^-$ is an inorganic or organic pharmaceutically acceptable anion, such as halide, phosphate, phosphite, carbonate, bicarbonate, sulphate, bisulfate, hydroxide, nitrate, persulfate, sulfite, sulphide, acetate, ascorbate, benzoate, citrate, dihydrogen citrate, hydrogen citrate, oxalate, succinate, tartrate, taurocholate, glycocholate, colate.

In one embodiment, the invention provides a process for preparing cross-linked polymers or salts thereof comprising a repeating unit of Formula (I) and/or Formula (II), as defined above, by reacting allylamine in presence of an acid with the cross-linking agent of Formula (IV) or a salt thereof, and a suitable radical initiator in at least a suitable solvent.

In another embodiment, the invention provides a process for preparing cross-linked polymers or salts thereof comprising a repeating unit of Formula (I), and/or Formula (II), as defined above, by reacting allylamine in presence of an acid with the cross-linking agent of Formula (IV) or a salt thereof, a suitable radical initiator and a suitable surfactant in a suitable mixture of solvents.

The process of this invention allow to synthesize the cross-linked poly(allylamine) polymers or salts thereof with a lower energy required for agitation during the polymerization and purification steps. Improved chemical homogeneity of the final product, easier and more efficient removal of the unreacted monomers are then obtained.

In a further embodiment, the invention provides a process for the preparation of carbonate salts of cross-linked poly(allylamine) polymers.

In another embodiment, the invention provides a cross-linked polymer or a salt thereof made by the process according to the present invention.

In another embodiment, the invention provides a cross-linked polymer or a salt thereof made by the process according to the present invention, where the desired content of salt, may be obtained by treating the cross-linked poly(allylamine) polymers with a base, such as NaOH, Na$_2$CO$_3$, NaHCO$_3$, KOH, K$_2$CO$_3$, KHCO$_3$.

In another embodiment, the invention provides a carbonate salt of a cross-linked polymer made by the process according to the present invention.

The process disclosed in the present invention provides straight a solid cross-linked polymer or a salt thereof with a particle size distribution of a defined dimension.

In another embodiment, the invention provides a population of particulate cross-linked polymer or a salt thereof obtained with the process of the invention with at least 90% by weight of the particles having a size lower than 350 μm, preferably lower than 300 μm, more preferably lower than 260 μm, more and more preferably lower than 200 μm, optionally together with at least one pharmaceutically acceptable excipient.

In another embodiment, the invention provides a population of particulate carbonate salt of the cross-linked polymer obtained according to the process of the invention wherein the content of chloride ions is lower than 0.1% and with a phosphate binding capacity comprised between 16 and 18 mEq/g.

In another embodiment, the invention provides the use of a cross-linked polymer or a salt thereof made by the process according to the present invention, for the manufacture of a medicament for removing phosphate from a subject and/or for the treatment of metabolic acidosis.

In another embodiment, the invention provides the use of the carbonate salt of a cross-linked polymer made by the process according to the present invention, for the manufacture of a medicament for removing phosphate and/or for the treatment of metabolic acidosis.

In another embodiment, the invention provides the use of a cross-linked polymer or a salt thereof made by the process according to the present invention, as intermediate in the synthesis of Colesevelam.

In another embodiment, the invention provides the use of a cross-linked polymer or a salt thereof made by the process of the present invention as intermediate for the manufacture of a medicament for removing bile salts from a subject.

In another embodiment, the invention provides a pharmaceutical preparation comprising the cross-linked polymer or a salt thereof obtained with the process of the invention with at least 90% by weight of the particles having a size lower than 350 μm, preferably lower than 300 μm, more preferably lower than 260 μm, more and more preferably lower than 200 μm, optionally together with at least one pharmaceutically acceptable excipient.

This invention also relates to a novel compound of Formula (IV), or a hydrate, solvate, or salt thereof, useful as co-monomer and/or cross-linking agent,

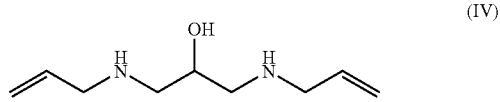

(IV)

wherein the salt is an inorganic or organic salt, or combination thereof, such as halide, phosphate, phosphite, carbonate, bicarbonate, sulphate, bisulfate, hydroxide, nitrate, persulfate, sulfite, sulphide, acetate, ascorbate, benzoate, citrate, dihydrogen citrate, hydrogen citrate, oxalate, succinate, tartrate, taurocholate, glycocholate, cholate.

In another embodiment, the invention provides a process for preparing a compound of Formula (IV) or a hydrate, solvate, or salt thereof, comprising: reacting a compound of Formula (V),

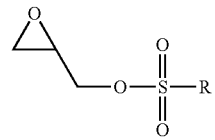

(V)

wherein R is methyl, p-tolyl, naphtyl;
or reacting a compound of formula (VI),

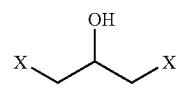

(VI)

wherein X is chlorine, bromine, iodine;
with allylamine in at least a suitable solvent, at a suitable temperature.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "polymerization" is used in terms of meanings implying not only homopolymerization but also copolymerization, and also there is the case where the term "polymer" is used in terms of meanings implying not only a homopolymer, but also a copolymer.

The term "repeating unit" refers to a portion of a polymer chain derived from a single molecule of monomer.

The term "cross-link or cross-linked" refers to an interconnection between polymer chains.

The term "cross-linking agent" refers to an agent which induces cross-linking, branching or a combination thereof to occur.

The term "poly(allylamine)" refers to a portion of a polymer comprising a repeating unit of Formula (I),

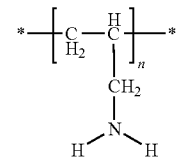

(I)

and/or Formula (II),

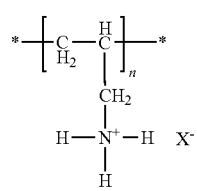

(II)

wherein n is an integer and X$^-$ is an inorganic or organic pharmaceutically acceptable anion, such as halide, phosphate, phosphite, carbonate, bicarbonate, sulphate, bisulfate, hydroxide, nitrate, persulfate, sulfite, sulphide, acetate, ascorbate, benzoate, citrate, dihydrogen citrate, hydrogen citrate, oxalate, succinate, tartrate, taurocholate, glycocholate, cholate.

The term "inorganic or organic peroxide" refers to hydrogen peroxide, potassium or ammonium persulfate and the like, and to aromatic or aliphatic peroxide, such as dicumyl-, dibenzyl-, di-tert-butyl-, acetylacetone, methylethylketone peroxide and the like, respectively.

The term "azo-compound" refers to an organic molecule containing an aza group, such as azobisisobutyronitrile, 2,2'-azobis(2-amidinopropane)dihydrochloride, 2,2'-azobis[2-(2-imidazolin-2-yl]propane dihydrochloride, 2,2'-azobis[2-(5-methyl-2-imidazolin-2-yl]propane dihydrochloride and the like.

The term "halide" refers to bromide, chloride, fluoride and iodide anion, preferably bromide, chloride.

The term "lower alcohol" refers to straight chain or branched alkyl residues containing 1 to 4 carbon atoms with one hydroxy group, such as methanol, ethanol, n-propanol, isopropanol, n-butanol, 1-butanol, 2-butanol, tert-butanol and the like.

The term "hydrate" refers to a solvate comprising a disclosed or claimed compound and a stoichiometric or non-stoichiometric amount of water.

The term "solvate" refers to a molecular complex comprising a disclosed or claimed compound and a stoichiometric or non-stoichiometric amount of one or more solvent molecules (e.g., EtOH).

The terms "emulsion" and "emulsion polymerization" are used hereafter, but they are non exclusive and refer also to other possible embodiments, such as suspension and suspension polymerization, or microemulsion and microemulsion polymerization.

The term "emulsion" refers to a mixture of two immiscible phases, where an oil phase is finely dispersed in a continuous water phase.

The term "emulsion polymerization" refers to a process wherein lipid-soluble polymers can be produced in a dispersed oil phase within a continuous water phase. The polymer formed remains in the dispersed oil droplets.

The term "inverse emulsion", "inverse suspension" and "inverse microemulsion" refer to an emulsion (suspension, microemulsion, respectively) where the continuous phase is an oil (a water-immiscible medium) and the dispersed phase is an aqueous solution, as opposed to conventional emulsions where an oil phase is finely dispersed in a continuous water phase.

The term "inverse emulsion polymerization" refers to a process wherein water-soluble polymers can be produced in a dispersed water phase within a continuous water-immiscible organic phase. The polymer formed remains in the dispersed water droplets and does not significantly affect the viscosity of the emulsion.

The term "surfactant" refers to wetting agents that change the surface tension of a liquid, and lower the interfacial tension between two liquids, increasing the kinetic stability of emulsions.

The term "cross-link" refers to an interconnection between polymer chains.

The term "cross-linking agent" refers to an agent which induces cross-linking, branching or a combination thereof to occur.

The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a tablet, capsule, pill, powder, granule, pellet, lozenge, pastille, elixir, syrup, solution, suspension, emulsion, drop, lotion, spray, tincture, cream, ointment, gel, unguent, suppository and transdermal devices for oral, enteral, parenteral or topical administrations.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

As used herein, particle size refers to a number average particle size as measured by conventional particle size measuring techniques well known to those skilled in the art, such as sieve analysis and Malvern granulometry experiments.

The term "about" encompasses the range of experimental error that may typically occurs in a measurement.

The present invention provides a novel process for preparing cross-linked polymers or salts thereof comprising a repeating unit of Formula (I), and/or Formula (II), as defined above. The process of this invention is a one step process particularly suited for large scale preparation. It can be conducted by homogeneous (solution) polymerization (Method A) or by inverse emulsion polymerization, inverse suspension, or inverse microemulsion polymerization (Method B), where at least a surfactant is required.

In one embodiment, the invention provides a process for preparing cross-linked polymers or salts thereof comprising a repeating unit of Formula (I) and/or Formula (II), as defined above, which process comprises reacting the commercially available allylamine in presence of an acid with the novel cross-linking agent of Formula (IV), or a salt thereof, as defined above, and a suitable radical initiator in at least a suitable solvent (Method A).

For the process of this invention, the preferred salt of compound of Formula (IV) is dihydrochloride.

The cross-linking agent of Formula (IV)/allylamine ratio is from about 5% to about 50% by weight, preferably from about 10% to about 30% by weight.

The acid is an inorganic acid, such as hydrochloric, hydrobromic, sulfuric, nitric, phosphoric, phosphorous acid or the like. Preferably, the acid is hydrochloric acid. Preferably, the acid/allylamine ratio is at least 1:1 mole/mole.

Any radical initiator or combination of radical initiators known to those skilled in the art is suitable for the process of this invention. Azo-compounds, inorganic or organic peroxides, or other systems that may be activated either thermally or by a redox reaction may be used. Preferably, the radical initiator is an azo-compound, such as azobisisobutyronitrile, 2,2'-azobis(2-amidinopropane)dihydrochloride, 2,2'-azobis[2-(2-imidazolin-2-yl]propane dihydrochloride, 2,2'-azobis[2-(5-methyl-2-imidazolin-2-yl]propane dihydrochloride; more preferably, the aza-compound are 2,2'-azobis(2-amidinopropane)dihydrochloride and/or 2,2'-azobis[2-(2-imidazolin-2-yl)propane]dihydrochloride; still more preferably, the aza-compound is 2,2'-azobis[2-(2-imidazolin-2-yl)propane]dihydrochloride.

Any suitable solvent known to those skilled in the art can be used for the process of the present invention.

For Method A, a suitable solvent is water or an organic solvent and/or a mixture thereof. A suitable organic solvent is a solvent miscible with water (e.g., lower alcohols, such as methanol, ethanol, propanol, isopropanol, tert-butanol; ethers, such as tetrahydrofuran, dioxane; ketones, such as acetone; polar aprotic solvents, such as acetonitrile, pyridine; etc.). Preferably, water or a mixture of water and acetonitrile are suitable solvents. More preferably, the polymerization is carried out in a mixture of water and acetonitrile.

Preferably, a solution of the allylamine and compound of Formula (IV) in water and acetonitrile is prepared in the desired ratio, where the overall concentration of allylamine is from about 20 to about 30 wt %.

Preferably, the ratio water/acetonitrile is of about 1:2.5 to about 1:3.5 volume/volume.

Preferably, water is added as aqueous 37% hydrochloric acid.

A suitable temperature is preferably comprised between the ten hours half-life decomposition temperature of the radical initiator used and the reflux temperature of the system.

When a mixture of water and acetonitrile is used, a cross-linked poly(allylamine) polymer or a salt thereof in a solid state as granular particles was obtained. When a solid is obtained from a reaction mixture, its isolation, recovery, purification, filtration, drying, etc. . . . are easier, than when a gel like substance was obtained. Mechanical or chemical processes that are used to transform a gel like substance in a solid state are not required.

The working up may be carried out generally using known procedures for the separation of the solid from the mother liquor, for example by filtration, with or without the assistance of pressure and/or vacuum, or by centrifugation, or by decantation.

With the process of the present invention, cross-linked polymers or salt thereof were obtained in the form of discrete, solid particles with at least 90% by weight of the particles having a size lower than 350 µm, preferably lower than 300 µm, more preferably lower than 260 µm, more and more preferably lower than 200 µm. For instance, in different experimental procedures solid particles with at least 90% by weight of the particles having a size of 300, 254, 245, 192 or 191 µm were obtained.

Drug powder particle size is an important factor in drug technology. If the particle size distribution is not uniform, the powder can segregate according to the different particle sizes, which may result in inaccurate dosing or inconsistent performance. A uniform particle size distribution insures better flowability, dissolution, compression quality, etc. A uniform particle size distribution insures an uniform dissolution rate if the powder is to dissolve, an uniform sedimentation rate if the powder is used in a suspension, and minimizes stratification when powders are stored or transported.

In another embodiment, the invention provides a process for preparing cross-linked polymers or salts thereof comprising a repeating unit of Formula (I) and/or Formula (II), as defined above, which process comprises reacting allylamine in presence of an acid with the cross-linking agent of Formula (IV), or a salt thereof, as defined above, a suitable radical initiator and at least a suitable surfactant in at least a suitable solvent (Method B), in an heterogeneous system consisting of a reversed phase emulsion, also known as a water-in-oil (w/o) type emulsion, hereinafter referred to as an inverse emulsion; or in an inverse suspension or in an inverse microemulsion.

Prior to the polymerization, the aqueous solution of the allylamine is emulsified in a suitable organic solvent with a suitable surfactant or mixture of surfactants. The resulting inverse emulsion can be stabilized and modified by a proper choice of the surfactant or mixture of surfactants.

Any surfactant known to those skilled in the art can be used for the process of the present invention. Suitable surfactants includes, but are not limited to non-ionic unsaturated or saturated fatty acid ester derivatives, such as fatty acid mono- or polyester of sorbitan, as exemplified by the commercially available Span family of surfactants, or fatty acid mono- or polyester of a polyethoxylated sorbitan, as exemplified by the commercially available Tween family of surfactants, or fatty acid mono- or polyester of glycerol; non-ionic polyethoxylated ether derivatives of a fatty alcohol, as exemplified by the commercially available Brij family of surfactants, or polyethoxylated ether derivatives of an alkylphenol, as exemplified by the commercially available Triton family of surfactants; cationic surfactants, such as a long hydrocarbon chain polyalkylammonium salt; or a mixture of them. Preferably, surfactants are non-ionic fatty acid ester derivatives, such as Span 85, Span 65, Span 60, Tween 60 and the like, and/or polyethoxylated ether of a fatty alcohol, such as Brij-58. More preferably, the surfactant is Span 85 and/or Brij-58.

For Method B, a suitable solvent is a mixture of solvents, preferably water and an organic solvent immiscible with the aqueous phase, providing that they does not present any reactivity with allylamine and their boiling point is higher than the polymerization temperature under atmospheric pressure. A specific gravity of the organic solvents not too different from that of the aqueous solution is preferable. Suitable solvents include, but are not limited to a low viscosity hydrocarbon, such as hexane, heptane, cyclohexane, toluene and the like; a chlorinated hydrocarbon, such as carbon tetrachloride, trichloroethylene, dichloromethane, chloroform, chlorobenzene and the like; or mixtures thereof. Preferred solvents include cyclohexane, toluene and chlorobenzene. More preferred solvents include cyclohexane, chlorobenzene. In case of the inverse microemulsion polymerization process, suitable solvents well known to those skilled in the art may be used as an alternative or as a third solvent to produce an inverse microemulsion. A suitable solvent is an alcohol, such as methanol or ethanol or the like. The inverse microemulsion is a thermodynamically stable colloidal system and it is generated spontaneously or with only little stirring to speed up the process, as opposed to a conventional inverse emulsion or inverse suspension.

The overall composition of the emulsion and the energy transferred to the system during the emulsification process influences the morphology, the average size and the size distribution of the droplets of aqueous solution dispersed in the organic medium, and the stability of the emulsion.

For increasing the conversion of the polymerization, sequential or semi-continuous addition of free radical initiator can carried out, to keep the steady state concentration of active free radicals at the same level throughout the long polymerization time.

Preferably, an aqueous solution of the allylamine and compound of Formula (IV) in the desired molar ratio, where the overall concentration of the allylamine is from about 20 to about 80 wt %, preferably from 50 to 70 wt %, is emulsified with a suitable organic solvent. The relative amount of the aqueous to the organic immiscible phases can be varied in a wide range, preferably the aqueous phase is between 30 and 50 vol %.

In the cross-linked poly(allylamine) polymers obtained with the process of the present invention, the basic groups may be salified. A cross-linked polymer with the desired content of salt, may be obtained by treating the cross-linked poly(allylamine) polymers with a suitable base, as well known to those skilled in the art. A suitable base is e.g. NaOH, $Na_2CO_3$, $NaHCO_3$, KOH, $K_2CO_3$, $KHCO_3$. Preferably, a suitable base is NaOH or $Na_2CO_3$.

According to a further general process, salts of compounds of Formula (I) and/or Formula (II) can be converted to alternative salts of Formula (I) and/or Formula (II), employing suitable ion interconversion techniques well known by a person skilled in the art.

In another embodiment, the invention provides a process for the preparation of a carbonate salt of a cross-linked poly (allylamine) polymer comprising:

a) dissolving sodium carbonate in water at a temperature from 30 to 40° C.;
b) adding an hydrochloride salt of the cross-linked poly(allylamine) polymer portion wise to the solution;
c) stirring the mixture obtained in b);
d) recovering the solid by filtration and re-suspending it in water;
e) filtering, washing and drying the carbonate salt of a cross-linked poly(allylamine) polymer.

Sodium carbonate is dissolved in water at a temperature from about 30 to 40° C. Preferably, the ratio sodium carbonate/water is of about 50 to 85 weight/volume, preferably 62.5 weight/volume.

An hydrochloride salt of the cross-linked poly(allylamine) polymer is added portion wise to this solution. Preferably, the ratio cross-linked poly(allylamine) polymer/sodium carbonate is of about 1.5 to 1.6 weight/weight. The mixture obtained in step b) is stirred for one hour, then the solid is recovered by filtration and re-suspending it in water for at least 20 minutes. Finally, the carbonate salt of the cross-linked poly(allylamine) polymer is recovered by methods well-known to those skilled in the art for the separation of the solid from the mother liquor, for example by filtration, with or without the assistance of pressure and/or vacuum, or by centrifugation, or by decantation. The collected solid is washed with water and dried by conventional methods well known to those skilled in the art, for example under reduced pressure, optionally by heating under reduced pressure. When Sevelamer hydrochloride is used, Sevelamer carbonate is obtained.

The particles of Sevelamer carbonate obtained with the process of the present invention have a low content of chloride ions, preferably the content of chloride ions is lower than 0.1%, and are obtained in the form of a not hygroscopic powder, with a controlled particle size. At least 90% by weight of the particles obtained have a size lower than 350 µm, preferably lower than 300 µm, more preferably lower than 260 µm, more and more preferably lower than 200 µm. Further preferably, 10% by weight of the particles obtained with the process of the present invention have a size lower than 20.8 µm. For instance, in different experimental procedures solid particles with at least 90% by weight of the particles having a size of 258, 246, 197 or 185 µm were obtained.

Sevelamer carbonate obtained with the process of the present invention also displays a phosphate binding capacity comprised between about 16 and 18 mEq/g.

With the process of the present invention, the polymerization of allylamine monomers with the novel compound of Formula (IV) or a salt thereof leads to cross-linked poly (allylamine) polymers with the same general chemical structure obtained with the prior art, but without the need of epichlorohydrin as cross-linking agent.

Other beneficial aspects of the present invention can be summarized:

a) it is a one step process, so it is a profitable, efficient, economic process, commercially useful;
b) a lower energy for agitation during the polymerization and purification steps is used: improved chemical homogeneity of the final product, easier and more efficient removal of the unreacted monomers from polymer particles are then obtained;
c) the energy transferred to the system during the emulsification process influences the morphology, the average size and the size distribution of the droplets of aqueous solution dispersed in the organic medium, and the stability of the emulsion;
d) the cross-linked poly(allylamine) polymers are obtained in the form of discrete, solid particles, with a particle size distribution of a defined dimension.

A population of particulate cross-linked polymer or a salt thereof with at least 90% by weight of the particles having a size lower than 350 µm, preferably lower than 300 µm, more preferably lower than 260 µm, more and more preferably lower than 200 µm, is obtained with this process, without need to additional milling, grinding, or other steps for reducing the particle size.

In another embodiment, the invention provides a population of particulate cross-linked polymer or a salt thereof made according to the process of the present invention with at least 90% by weight of the particles having a size lower than 350 µm, preferably lower than 300 µm, more preferably lower than 260 µm, more and more preferably lower than 200 µm, optionally together with at least one pharmaceutically acceptable excipient.

In another embodiment, the invention provides a cross-linked polymer or a salt thereof made by the process of the invention. Preferably the invention relates to Sevelamer or a salt thereof obtainable according to the present invention.

The invention relates also to the carbonate salts of the cross-linked polymer obtainable according to the present invention, preferably the invention relates to Sevelamer carbonate.

In another embodiment, the invention provides a cross-linked polymer or a salt thereof made by the process of the present invention for removing phosphate from a subject.

In another embodiment, the invention provides a carbonate salt of a cross-linked polymer made by the process of the present invention for removing phosphate and/or treating metabolic acidosis from a subject In another embodiment, the invention provides the use of a cross-linked polymer or a salt thereof, preferably carbonate, made according to the process of the present invention for the manufacture of a medicament for removing phosphate from a subject and/or for the treatment of metabolic acidosis.

In another embodiment, the invention provides a pharmaceutical preparation comprising the cross-linked polymer or a salt thereof, preferably carbonate, made according to the process of the present invention with at least 90% by weight of the particles having a size lower than 350 µm, preferably lower than 300 µm, more preferably lower than 260 µm, more and more preferably lower than 200 µm, optionally together with at least one pharmaceutically acceptable excipient.

The invention also relates to a pharmaceutical preparation comprising Sevelamer or a salt thereof, preferably carbonate, made according to the process of the invention, with at least 90% by weight of the particles having a size lower than 350 µm, preferably lower than 300 µm, more preferably lower than 260 µm, more and more preferably lower than 200 µm, optionally together with at least one pharmaceutically acceptable excipient. The fields of use, the dosage to be administered and appropriate forms of dosaging are known from and described, for example, in U.S. Pat. No. 5,496,545; U.S. Pat. No. 6,083,495, U.S. Pat. No. 6,509,013; U.S. Pat. No. 6,733,780; U.S. Pat. No. 6,858,203; U.S. Pat. No. 7,014,846; US 2006/171916; EP 1,379,258 B1.

Suitable pharmaceutically acceptable excipient are well known to those skilled in the art. Excipients include, by way of illustration and not limitation, diluents, fillers, agglutinants, disintegrants, disintegration inhibitors, absorption accelerators, binders, carriers, suspending/dispersing agents, film formers/coatings, adhesives, antiadherents, wetting agents, lubricants, glidants, preservatives, sorbents, surface active agents, antioxidants, substances added to mask or counteract a disagreeable taste or odour, flavourings, colorants, fragrances, aromatising agents, sweeteners and substances added to improve appearance of the composition.

A person skilled in the art is aware of a whole variety of such excipient compounds suitable to formulate a pharmaceutical composition. The choice of excipient will to a large extent depend on factors such as the particular mode of administration, the effect of the excipient on solubility and stability, and the nature of the dosage form.

Besides, the invention provides a process to prepare intermediates that are useful to prepare substrate-binding polymers useful in medicine, such as Colesevelam. In another embodiment, the invention provides the use of a cross-linked polymer or a salt thereof made by the process of the present invention as intermediate in the synthesis of Colesevelam.

In another embodiment, the invention provides the use of a cross-linked polymer or a salt thereof made by the process of the present invention as intermediate for the manufacture of a medicament for removing bile salts from a subject.

In another embodiment, the invention provides a compound, or a hydrate, a solvate, a salt thereof of Formula (IV)

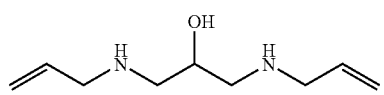

(IV)

that is useful as co-monomer and/or cross-linking agent. A salt of compound (IV) is as defined above. The preferred salt of compound of Formula (IV) is a dihydrochloride.

In another embodiment, the invention provides a process for preparing a compound of Formula (IV), or a hydrate, a solvate, a salt thereof, comprising reacting a compound of Formula (V),

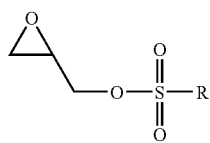

(V)

wherein R is methyl, p-tolyl, naphtyl;
or reacting a compound of Formula (VI),

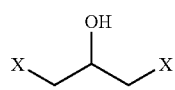

(VI)

wherein X is chlorine, bromine, iodine;
with allylamine in at least a suitable solvent, at a suitable temperature.

Any suitable solvent known to those skilled in the art can be used for preparing compound of Formula (IV). Suitable solvents include, but are not limited to, an hydrocarbon, such as toluene or the like; an alcohol, such as methanol or ethanol or the like; a chlorinated hydrocarbon, such as dichloromethane or chloroform or the like; an ester, such as ethyl acetate or the like; an ether, such as THF or dioxane or the like; a ketone, such as acetone or the like; a nitrile, such as acetonitrile or the like; an amide, such as N,N-dimethylformamide or the like; a sulfoxide, such as dimethylsulfoxide or the like; water, or mixtures thereof. Preferred solvents include an ether, preferably tetrahydrofuran, or a mixture of water and tetrahydrofuran.

Compounds of Formula (V) are prepared according to Sharpless K. B. et al, *J. Org. Chem.*, 1989, 54, 1295-1304.

Compounds of Formula (VI) are commercially available compounds.

The process to prepare compound of Formula (IV) is particularly suited for large-scale preparation.

Preferred compound of Formula (V) is the glycidyl tosylate (Va) (R=p-tolyl).

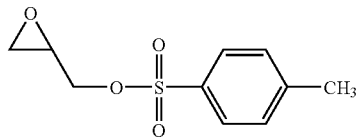

In a particular embodiment, a solution of glycidyl tosylate of Formula (Va) in tetrahydrofuran was added to a mixture of water and allylamine, at a suitable temperature. A suitable temperature is a temperature in order for the reaction to be complete. Preferred temperature is from about 55° C. to about 65° C. Preferably, the ratio glycidyl tosylate of Formula (Va)/allylamine is of about 1:2 to about 1:3 weight/weight. The resulting mixture was concentrated to residue. A suitable solvent and a suitable acid was added in order to recover a salt of compound of Formula (IV). A suitable solvent is an alcohol, preferably a lower alcohol. Examples of alcoholic solvents include, but are not limited to, isopropanol, 1-butanol, 2-butanol, tert-butanol; preferably, the alcoholic solvent is isopropanol.

A suitable acid is an inorganic or organic acid, such as hydrohalide acid, phosphoric acid, phosphorous acid, carbonic acid, hydrogen carbonate acid, sulfuric acid, hydrogen sulfuric acid, nitric acid, persulfuric acid, sulfurous acid, hydrogen sulfide acid, acetic acid, ascorbic acid, benzoic acid, citric acid, dihydrogen citric acid, hydrogen citric acid, oxalic acid, succinic acid, tartaric acid, taurocholic acid, glycocholic acid, cholic acid. Preferred acid is 37% aqueous hydrochloric acid.

A preferred temperature to precipitate a compound of Formula (IV) is comprised in a range of about 5° C. to 10° C. The compound of Formula (IV) was recovered by methods well-known to those skilled in the art for the separation of the solid from the mother liquor, for example by filtration, with or without the assistance of pressure and/or vacuum, or by centrifugation, or by decantation. The collected solid is washed with at least a suitable solvent and dried by conventional methods well known to those skilled in the art. Compound of Formula (IV) can be used in the next step without further purification.

One skilled in the art will appreciate that by adjusting concentration, temperature and time the yield of compound of Formula (IV) may be optimized.

According to a further general process, salts of compounds of Formula (IV) can be converted to alternative salts of Formula (IV) employing suitable ion interconversion techniques well known by a person skilled in the art. Salts of compounds of Formula (IV) can be converted to a corresponding base by treating them with a suitable base, such as NaOH, as well known to those skilled in the art.

While the present invention has been described in terms of its specific embodiments, certain modifications and equivalents will be apparent to those skilled in the art and are included within the scope of the present invention.

In the following, the present invention shall be illustrated by means of some examples, which are not construed to be viewed as limiting the scope of the invention.

EXAMPLES

The following abbreviations refer respectively to the definitions below:

THF (tetrahydrofuran), TLC (thin layer chromatography), VA-044 (2,2'-azobis[2-(2-imidazolin-2-yl)propane]dihydrochloride) and V-50 (2,2'-azobis(2-amidinopropane)dihydrochloride), both from Wako Chemicals.

Surfactant Brij-58 is an oligooxyethylene hexadecyl ether with 20 ethyleneoxide repeat units, supplied by Sigma-Aldrich.

Surfactant Span-85 is a sorbitan trioleate, supplied by Sigma-Aldrich.

The TLC and NMR data provided in the examples described below are obtained as follow:

TLC was performed on silica gel with fluorescent indicator 254 nm, 5-17 µm, medium pore diameter 60 Å.

$^1$H NMR spectra were performed on a Jeol Eclipse 300, using $D_2O$ as solvent. The chemical shifts are reported in δ ppm relative to TMS.

Phosphate binding assay was carried out according to J. R. Mazzeo et al., *Journal of Pharmaceutical and Biomedical Analysis*, 19 (1999) 911-915. The assay developed for this purpose involves mixing the polymer with a solution of known phosphate concentration, filtering off the polymer-phosphate adduct, and quantification of the unbound phosphate concentration by ion chromatography. The binding capacity is expressed as mEq/g.

Example 1

Preparation of 1,3-bis-allylamino-2-propanol (IV), dihydrochloride salt

A 1 L four-necked flask, equipped with a mechanical stirrer, temperature probe, dropping funnel and a condenser topped with a nitrogen gas inlet, was charged with allylamine (321 g, 5.62 mol) and water (46 mL). The resulting mixture was heated to 57° C. and, while maintaining a vigorous stirring, a solution of glycidyl tosylate (Va) (128 g, 0.561 mol) in THF (128 mL) was added dropwise. When the addition of (Va) was complete, the reaction was allowed to stir at 62° C. for 45 minutes. The reaction progress and/or completion was monitored by TLC for the disappearance of (Va) (eluent: n-hexane/ethyl acetate 7:3 volume/volume). The reaction mixture was concentrated to residue under reduced pressure, isopropanol (700 mL) was added and the pH of the solution was adjusted to 1-1.5 by adding aqueous hydrochloric acid (37%, 148 mL). While stirring, the mixture was cooled to 5° C., and the solid was filtered and washed three times with isopropanol (100 mL). The product was further dried under reduced pressure at 60° C. to afford the compound (IV) (65.4 g) as a white solid, which was used in the next step without further purification.

Overall yield: 48%.
Melting point: 323-325° C.
Elemental analysis: C, 44.4%; H, 8.36%; N, 11.4%; Cl, 27.7%; O, 7.96%.
$^1$H NMR ($D_2O$): δ 5.93-5.84 (m, 2H), 5.53-5.47 (t, 4H), 4.27-4.22 (m, 1H), 3.71-3.69 (d, 4H), 3.24-3.02 (m, 4H).

Example 2

Preparation of Sevelamer Hydrochloride (III)

Method A

A 250 mL jacketed reaction vessel, equipped with a mechanical stirrer, temperature probe, dropping funnel and a condenser topped with a nitrogen gas inlet, was charged with 37% hydrochloric acid (27.6 g, 0.280 mol), and the solution was cooled to 0° C. Allylamine (16 g, 0.280 mol) was added dropwise while stirring, maintaining the temperature from 5 to 10° C. After the addition was complete, acetonitrile (52.2 mL) and 1,3-bis-allylamino-2-propanol dihydrochloride (IV) (8.3 g, 0.034 mol) were added. The solution was heated to 50° C. and the azo-initiator VA-044 (1.15 g) was added. The reaction was allowed to stir at 50° C. for 24 hours. VA-044 (1.15 g) was added again and the heating and stirring was continued for additional 18 hours. Then the solid was filtered off, washed with methanol (150 mL) and dried under reduced pressure at 40° C. to afford a granular, pale-yellow solid (27 g), with a phosphate binding capacity of 13.6 mEq/g.

Example 3

Preparation of Sevelamer Hydrochloride (III)

Method A

A 250 mL jacketed reaction vessel, equipped with a mechanical stirrer, temperature probe, dropping funnel and a condenser topped with a nitrogen gas inlet, was charged with 37% hydrochloric acid (55.3 g, 0.561 mol), and the solution was cooled to 0° C. Allylamine (32 g, 0.561 mol) was added dropwise while stirring, maintaining the temperature from 5 to 10° C. After the addition was complete, the liquid (12 ml) was removed by distillation under reduced pressure at 60-70° C. The solution was cooled to 50° C., 1,3-bis-allylamino-2-propanol dihydrochloride (IV) (16 g, 0.067 mol) and the azo-initiator VA-044 (1.15 g), suspended in water (2.5 mL), were added. The reaction was allowed to stir at 50° C. for 24 hours. VA-044 (1.15 g) suspended in water (2.5 mL) was added again and the heating and stirring was continued for additional 18 hours. The reaction mixture was added with methanol (1 L), and the solid was filtered and suspended in water together with NaOH (3 g). The solid was filtered again and rinsed by suspending it in isopropanol (1 L). The mixture was stirred for an hour, and finally the solid was collected by filtration. The product was dried under reduced pressure at 40° C. to afford a granular, pale-yellow solid (26 g), with a phosphate binding capacity of 14.7 mEq/g.

Example 4

Preparation of Sevelamer Hydrochloride (III)

Method B

A 50 mL flask, equipped with a magnetic stirrer, temperature probe, dropping funnel and a condenser topped with a nitrogen gas inlet, was charged with 37% hydrochloric acid (4.22 g, 0.043 mol), and the solution was cooled to 0° C. Allylamine (2.44 g, 0.043 mol) was added dropwise while stirring, maintaining the temperature from 5 to 10° C. After the addition was complete, the liquid (12 ml) was removed by distillation under reduced pressure at 60-70° C. Then 1,3-bis-allylamino-2-propanol dihydrochloride (IV) (0.82 g, 0.0034 mol), the surfactant Brij-58 (0.064 g), and the azo-initiators VA-044 and V-50 (a total of 0.12 g in a 1/1 weight ratio) were dissolved in HPLC-grade water (3.5 mL). In a separate batch, the surfactant Span-85 (0.312 g) was dissolved in cyclohexane (4.8 mL). The resulting oil phase is mixed with the aqueous phase, homogenised with a Ultra Turrax (15 minutes at 22000 rpm), and then charged in a schlenk tube as the polymerization reactor. In the following, the emulsion is deoxygenated by purging nitrogen for 20 min, then the reaction tube is fitted with a mechanical stirrer, immersed in a thermostated oil bath and the polymerization is started by raising the temperature to 44° C. while stirring at 200 rpm. After 24 hours of stirring at this temperature, the oil bath is heated to 56° C. and the polymerization is continued for another 24 hours. The viscosity of the emulsion increases during the polymerization, with a significant increase occurring after the start of the second stage, resulting in the rapid gelification of the polymerization mixture. At the end of the polymerization the resulting semi-transparent and apparently homogeneous and monolithic gel-like material can be easily redispersed by addition of a large excess of water, resulting in the inversion of the emulsion and in the formation of a milky dispersion of swollen microgel particles with a spherical appearance and diameter of 5 to 100 μm according to a simple observation by optical microscopy. The cross-linked polymer gel is purified from the unreacted monomers and initiator ad other impurities by coagulation from the concentrated aqueous dispersion in a large excess of methanol, followed by several washings with isopropanol. The gel collected by filtration and drying under reduced pressure at 40° C. to afford a white powder (1.92 g), with a phosphate binding capacity of 13.2 mEq/g.

Example 5

Preparation of Sevelamer Carbonate

A 5 L reactor, equipped with a mechanical stirrer, temperature probe, dropping funnel and a condenser topped with a nitrogen inlet, was charged with water (4 L), sodium carbonate (250 g), and the solution was brought at 35° C. Sevelamer hydrochloride (400 g) are added portion wise for 1 h, in portions of 20 g each, while stirring, maintaining the temperature from 30 to 35° C. The solid is then filtered and suspended in water (3 L), at 30-35° C. The mixture is allowed to stir for 20 minutes. The solid was filtered again and rinsed with water until disappearance of chloride ions. The product is dried under reduced pressure at 70° C. to afford Sevelamer carbonate (290 g), with a phosphate binding capacity of 17.2-17.6 mEq/g.

Elemental analysis:

C, 49.3%; H, 9.5%; N, 13.7%; O, 27.5%; Cl, <0.1%.

The invention claimed is:

1. A process for preparing cross-linked polymers or salts thereof comprising a repeating unit of Formula (I),

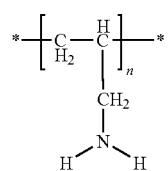

and/or Formula (II),

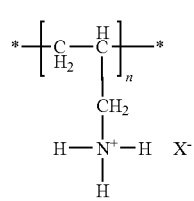

wherein n is an integer and X⁻ is an inorganic or organic pharmaceutically acceptable anion, which process comprises:

reacting allylamine in presence of an acid with the cross-linking agent of Formula (IV)

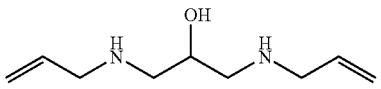

or a salt thereof, and a suitable radical initiator in at least a suitable solvent.

2. The process according to claim 1, wherein X⁻ is selected from the group consisting of halide, phosphate, phosphite, carbonate, bicarbonate, sulphate, bisulfate, hydroxide, nitrate, persulfate, sulfite, sulphide, acetate, ascorbate, benzoate, citrate, dihydrogen citrate, hydrogen citrate, oxalate, succinate, tartrate, taurocholate, glycocholate, and cholate, and the salt of compound of Formula (IV) is an inorganic or organic salt selected from the group consisting of halide, phosphate, phosphite, carbonate, bicarbonate, sulphate, bisulfate, hydroxide, nitrate, persulfate, sulfite, sulphide, acetate, ascorbate, benzoate, citrate, dihydrogen citrate, hydrogen citrate, oxalate, succinate, tartrate, taurocholate, glycocholate, and cholate.

3. The process according to claim 2, wherein said salt is dihydrochloride.

4. The process according to claim 1, wherein the cross-linking agent of Formula (IV)/allylamine ratio is from about 5% to about 50% wt %.

5. The process according to claim 1, wherein the radical initiator is an azo-compound or an inorganic or organic peroxide.

6. The process according to claim 1, wherein the solvent is a mixture of water/acetonitrile.

7. The process according to claim 1, further comprising adding to the reaction mixture at least a suitable surfactant.

8. The process according to claim 1, further comprising treating the cross-linked poly(allylamine) polymers with a base.

9. The process according to claim 4, wherein the process further comprises providing cross-linking agent of Formula (IV)/allylamine at a ratio of from about 30 to about 50 wt %, and the cross-linked polymer is Sevelamer.

10. The process according to claim 9, wherein particles are obtained and at least 90% by weight of the particles obtained have a size lower than 350 μm.

11. The process according to claim 4, wherein the cross-linking agent of Formula (IV)/allylamine ratio is from about 10% to about 30% wt %.

12. The process according to claim 4, wherein the cross-linking agent of Formula (IV)/allylamine ratio is from about 20% to about 30% wt %.

13. The process according to claim 8, wherein the base is NaOH, Na₂CO₃, NaHCO₃, KOH, K₂CO₃, or KHCO₃.

14. The process according to claim 8, wherein the base is NaOH or Na₂CO₃.

15. The process according to claim 10, wherein at least 90% by weight of the particles obtained have a size lower than 300 μm.

16. The process according to claim 10, wherein at least 90% by weight of the particles obtained have a size lower than 260 μm.

17. The process according to claim 10, wherein at least 90% by weight of the particles obtained have a size lower than 200 µm.

18. The process according to claim 1, wherein the cross-linked polymer is sevelamer, the process comprising the following steps:
  (i) mixing hydrochloric acid, allylamine, and acetonitrile,
  (ii) adding the cross-linking agent of Formula (IV) in the form of its dihydrochloride salt,
  (iii) adding 2,2'-azobis[2-(2-imidazolin-2-yl)propane]dihydrochloride as the radical initiator and heating the reaction mixture up 50° C. over a period of 24 hours;
  (iv) adding 2,2'-azobiz[2-(2-imidazolin-2-yl)propane]dihydrochloride and maintaining the temperature over an additional period of 18 hours;
  (v) filtering, washing and drying the obtained solid;
  wherein the ratio of the cross-linking agent of Formula (IV) in the form of free base and allylamine is about 36 wt %.

19. The process according to claim 9, further comprising alkylating the resulting cross-linked polymer or salt thereof with 1-bromodecane and (6-bromohexyl)-trimethylammonium bromide.

* * * * *